United States Patent
Sheu et al.

(10) Patent No.: US 12,409,088 B2
(45) Date of Patent: Sep. 9, 2025

(54) INTEGRATED AUTOMATIC TURNING BED SYSTEM

(71) Applicant: AEROSPACE INDUSTRIAL DEVELOPMENT CORPORATION, Taichung (TW)

(72) Inventors: Jinn-Biau Sheu, Taichung (TW); Kun-Chi Tsai, Taichung (TW); Fu-Kang Lu, Taichung (TW); Hao-Jen Kao, Taichung (TW)

( * ) Notice: Subject to any disclaimer, the term of this patent is extended or adjusted under 35 U.S.C. 154(b) by 160 days.

(21) Appl. No.: 18/389,811

(22) Filed: Dec. 20, 2023

(65) Prior Publication Data
US 2025/0073103 A1   Mar. 6, 2025

(30) Foreign Application Priority Data
Sep. 1, 2023  (TW) ................................. 112133317

(51) Int. Cl.
*A61G 7/018*  (2006.01)
*A61G 7/057*  (2006.01)
*A61G 9/00*   (2006.01)
*A61G 9/02*   (2006.01)

(52) U.S. Cl.
CPC .......... *A61G 7/018* (2013.01); *A61G 7/0573* (2013.01); *A61G 9/003* (2013.01); *A61G 9/02* (2013.01); *A61G 2203/34* (2013.01)

(58) Field of Classification Search
CPC .......... A61G 7/00; A61G 7/0573; A61G 7/02; A61G 2203/30; A61G 7/057; A61G 7/002; G06Q 10/063; G06Q 50/22; A61B 5/1115; A61B 5/1114; A61B 5/1116; A61B 5/447; A61B 5/7264; A61B 5/6892; G16H 40/63; G16H 40/67; G16H 50/70; G06N 20/00; A61F 5/48
See application file for complete search history.

(56) References Cited

U.S. PATENT DOCUMENTS 5,269,030 A  *  12/1993  Pahno  ..................... A61G 7/02
4/615
2024/0225558 A1*  7/2024  Ishikawa  ................ G06Q 50/22

FOREIGN PATENT DOCUMENTS

TW   I297266 B   6/2008
TW   M621079 U   12/2021

* cited by examiner

*Primary Examiner* — Fredrick C Conley
(74) *Attorney, Agent, or Firm* — Bruce Stone LLP; Joseph A. Bruce

(57) ABSTRACT

An integrated automatic turning bed system is provided. The system integrates the system controller with subsystems such as an electric turning bed, a pressure-sensing mattress, and/or an electronic diaper machine, and achieves comprehensive care for incapacitated bedridden people through automation and intelligence. By utilizing subsystem sensing and system controller to control and ensure the stability, reliability, and control accuracy of the system, the safety and comfort of the bedridden people can be ensured and care services are improved, which also effectively reduces the burden on caregivers at the same time.

18 Claims, 13 Drawing Sheets

Electronic whiteboard
Present time: 01.03.2021 8:00AM                                                   E1

| | Bed No. 1 | | | |
|---|---|---|---|---|
| ON | Patient turned over | No excrement | No suctioning | |
| Turn executed | Bed in tilted position | No flushing | Patient in bed | |

First turn

| | Bed No. 2 | | | |
|---|---|---|---|---|
| ON | Patient turned over | No excrement | No suctioning | |
| Turn executed | Bed in flat position | No flushing | Patient in bed | |

Patient turned over

| | Bed No. 3 | | | |
|---|---|---|---|---|
| OFF | Patient lying flat | With excrement | No suctioning | |
| Turn executed | Bed in flat position | No flushing | Patient in bed | |

With excrement

FIG.6A

Electronic whiteboard
Present time: 01.03.2021 8:00AM  E1

| Bed No. 4 | | | |
|---|---|---|---|
| OFF | Patient lying flat | No excrement | No suctioning |
| Turn executed | Bed in flat position | No flushing | Patient out of bed |

Patient out of bed

| Bed No. 5 | | | |
|---|---|---|---|
| ON | Patient lying flat | With excrement | No suctioning |
| Turn executed | Bed in flat position | Flushing | Patient in bed |

Flushing

| Bed No. 6 | | | |
|---|---|---|---|
| ON | Patient lying flat | With excrement | Suctioning |
| Turn executed | Bed in flat position | No flushing | Patient in bed |

Suctioning

FIG.6B

| Bed No. 3 | Time | Current status | AUTO | Patient status | Bed surface | Excrement | Flushed | Suctioned | Patient in bed |
|---|---|---|---|---|---|---|---|---|---|
| 2023/3/1 | 14:30 | | ON | Lying flat | Flat position | No | No | No | In bed |
| 2023/3/1 | 14:31 | Executed AUTO turn, 5th Turn | ON | Turned over | Tilted position | No | No | No | In bed |
| 2023/3/1 | 14:32 | | ON | Turned over | Tilted position | No | No | No | In bed |
| 2023/3/1 | 14:33 | Turn completed | ON | Turned over | Tilted position | No | No | No | In bed |
| 2023/3/1 | 14:34 | | ON | Lying flat | Flat position | No | No | No | In bed |
| 2023/3/1 | 14:35 | | ON | Lying flat | Flat position | No | No | No | In bed |
| 2023/3/1 | 14:36 | | ON | Lying flat | Flat position | No | No | No | In bed |
| 2023/3/1 | 14:37 | Patient turn detected | ON | Turned over | Flat position | No | No | No | In bed |
| 2023/3/1 | 14:38 | | ON | Turned over | Flat position | No | No | No | In bed |
| 2023/3/1 | 14:39 | | ON | Turned over | Flat position | No | No | No | In bed |
| 2023/3/1 | 14:40 | Excrement detected and patient turned, alert sound issued for caregiver to assist in laying down | ON | Turned over | Flat position | Yes | No | No | In bed |
| 2023/3/1 | 14:41 | | ON | Turned over | Flat position | Yes | No | No | In bed |
| 2023/3/1 | 14:42 | | ON | Turned over | Flat position | Yes | No | No | In bed |
| 2023/3/1 | 14:43 | | ON | Turned over | Flat position | Yes | No | No | In bed |
| 2023/3/1 | 14:44 | Patient laying flat detected, suctioned | ON | Lying flat | Flat position | Yes | No | Yes | In bed |
| 2023/3/1 | 14:45 | | ON | Lying flat | Flat position | Yes | No | Yes | In bed |
| 2023/3/1 | 14:46 | | ON | Lying flat | Flat position | Yes | No | Yes | In bed |

FIG.11A

| Bed No. 3 | Time | Current status | AUTO | Patient status | Bed surface | Excrement | Flushed | Suctioned | Patient in bed |
|---|---|---|---|---|---|---|---|---|---|
| 2023/3/1 | 14:47 | Suction stopped | ON | Lying flat | Flat position | Yes | No | No | In bed |
| 2023/3/1 | 14:48 | Water drained | ON | Lying flat | Flat position | Yes | Yes | No | In bed |
| 2023/3/1 | 14:49 | | ON | Lying flat | Flat position | Yes | Yes | No | In bed |
| 2023/3/1 | 14:50 | | ON | Lying flat | Flat position | Yes | Yes | No | In bed |
| 2023/3/1 | 14:51 | No excrement detected, flush stopped | ON | Lying flat | Flat position | No | No | No | In bed |
| 2023/3/1 | 14:52 | | ON | Lying flat | Flat position | No | No | No | In bed |
| 2023/3/1 | 14:53 | | ON | Lying flat | Flat position | No | No | No | In bed |
| 2023/3/1 | 14:54 | AUTO Canceled | OFF | Lying flat | Flat position | No | No | No | In bed |
| 2023/3/1 | 14:55 | | OFF | Lying flat | Flat position | No | No | No | In bed |
| 2023/3/1 | 14:56 | Turn executed, 6th Turn | OFF | Turned over | Tilted position | No | No | No | In bed |
| 2023/3/1 | 14:57 | | OFF | Turned over | Tilted position | No | No | No | In bed |
| 2023/3/1 | 14:58 | Turn completed | OFF | Turned over | Tilted position | No | No | No | In bed |
| 2023/3/1 | 14:59 | | OFF | Lying flat | Flat position | No | No | No | In bed |
| 2023/3/1 | 15:00 | Patient off bed detected | OFF | Lying flat | Flat position | No | No | No | Out of bed |
| 2023/3/1 | 15:01 | Patient off bed detected | OFF | Lying flat | Flat position | No | No | No | Out of bed |

FIG.11B

INTEGRATED AUTOMATIC TURNING BED SYSTEM

BACKGROUND

Field of the Invention

The present invention relates to the technical field of care devices and systems, and more particularly to an integrated automatic turning bed system that includes an electric turning bed, a pressure-sensing mattress, and/or an electronic diaper machine.

Description of Related Art

In the global society, with the improvement of living conditions and the advancement of medical technology, the lifespan of the population is significantly increasing. However, this also brings about the problem of population aging, especially in developed countries and regions. The aging society has brought about an increasing demand for medical and care services, accompanied by a shortage of medical manpower and limited family care capabilities. At the same time, the trend of fewer children in the population is becoming more pronounced, exacerbating the pressure on care services.

Generally speaking, patients or elderly bedridden people need to roll over regularly to prevent pressure ulcers, and they also need to change diapers promptly to maintain personal cleanliness and hygiene. However, due to a shortage of care manpower, it is often difficult to ensure that these necessary care tasks can be completed promptly and appropriately. On the other hand, due to the change of caregivers, there may be inconsistencies in care methods, leading to a decrease in the comfort and quality of life of patients or the elderly.

In addition, some incapacitated people who are cared for may not receive timely and appropriate care during the caregiver changing period, such as turning over, changing diapers, and cleaning, which may have adverse effects on their physical and mental health. Due to the existence of these issues, the quality and effectiveness of care services are often limited, and the cost of care and work stress are increased.

SUMMARY

To overcome the above technical problems, the objective of the present invention is to provide an integrated automatic turning bed system. The system of the present invention integrates the system controller with subsystems such as an electric turning bed, a pressure-sensing mattress, and/or an electronic diaper machine, and achieves comprehensive care for incapacitated bedridden people (or patient) through automation and intelligence. By utilizing subsystem sensing and system controller to control and ensure the stability, reliability, and control accuracy of the system, the safety and comfort of the bedridden people can be ensured and care services are improved, which also effectively reduces the burden on caregivers at the same time.

To achieve the above objective, an integrated automatic turning bed system provided by the invention comprises a system controller and a plurality of subsystems connected to the system controller; wherein the system controller includes a central processing unit (CPU), and a system memory and an AI deep learning module connected to the CPU; the system memory includes a bedridden person database, a movement analysis database, and a movement module database;

the subsystems include at least one electric turning bed, at least one pressure-sensing mattress, and at least one electronic diaper machine, which are connected to the CPU, respectively;

wherein, the system controller is used to receive and store status feedback data from the electric turning bed, the pressure-sensing mattress, and the electronic diaper machine, the system controller sends out task execution signals to the electric turning bed, the pressure-sensing mattress, and the electronic diaper machine after calculation based on the status feedback data, in order to drive the subsystems to act according to the task execution signals;

the AI deep learning module is used to read the bedridden person database, the movement analysis database, and the movement module database and perform calculations and learning based on the bedridden person database, the movement analysis database, and the movement module database, so as to output and store an AI recommended turning module that is suitable for the current needs of a bedridden person, for prompting caregivers to adapt to the turning mode of the bedridden person.

In an embodiment of the present invention, the electric turning bed includes a main frame, an actuating device, a lifting base frame, and a tilting frame; the main frame includes twelve sub-frames; the twelve sub-frames of the main frame are a back frame, a seat frame, a leg frame, and a foot frame corresponding to respective parts of the human body, as well as two back side frames, two seat side frames, two leg side frames, and two foot side frames disposed at two sides of the respective part-frames; the tilting frame is located on the back frame, the lifting base frame is located below the main frame, the actuating device includes twelve main-frame actuators independently connected to the twelve sub-frames, a base-frame actuator independently connected to the lifting base frame, and a tilting-frame actuator independently connected to the tilting frame; each of the main-frame actuators, the base-frame actuator, and the tilting-frame actuator includes a frame motion sensing unit to detect and output status feedback data corresponding to the twelve sub-frames of the main frame, the lifting base frame, and the tilting frame; the CPU is connected to the frame motion sensing units, the main-frame actuators, the base-frame actuator, and the tilting-frame actuator; so that the CPU receives the status feedback data and outputs task execution signals to drive the main-frame actuators, the base-frame actuators, and/or the tilting-frame actuators to operate.

In an embodiment of the present invention, the status feedback data output from the main-frame actuators, the base-frame actuators, and/or the tilting-frame actuators include displacement distance and/or displacement angle of the twelve sub-frames of the main frame, the lifting base frame, and the tilting frame; so that the CPU outputs, by calculation based on the displacement distance and/or displacement angle, task execution signals to drive the main frame, the lifting base frame, and the tilting frame to operate.

In an embodiment of the present invention, the pressure-sensing mattress is disposed on the electric turning bed, and the pressure-sensing mattress is a foldable mattress and includes twelve cushions correspondingly disposed to the twelve sub-frames of the main frame, inside each of the twelve cushions is provided a pressure sensor to detect and output status feedback data corresponding to the twelve cushions; the CPU obtains biometric data of the bedridden person based on the status feedback data; so that the CPU outputs, by calculation based on the biometric data, task execution signals to drive the main frame, the lifting base frame, and the tilting frame to operate.

In an embodiment of the present invention, the status feedback data from the respective pressure sensors include pressure sensing data of the twelve cushions; so that the CPU calculates the biometric data of the bedridden person based on the status feedback data, and the CPU calculates and outputs task execution signals that drive the main frame, the lifting base frame, and/or the tilting frame to operate.

In an embodiment of the present invention, the status feedback data from the respective pressure sensors include pressure sensing data of the twelve cushions; the pressure-sensing mattress includes a pressure state analysis module connected to the respective pressure sensors, the pressure state analysis module calculates and outputs the biometric data of the bedridden person based on the pressure sensing data, and the CPU receives and outputs task execution signals that drive the main frame, the lifting base frame, and/or the tilting frame to operate based on the biometric data.

In an embodiment of the present invention, the biometric data include the pressure values of the cushions of the pressure-sensing mattress, and respiratory frequency, heartbeat frequency, sleep analysis, and long-lying analysis of the bedridden person.

In an embodiment of the present invention, the electronic diaper machine includes a bedpan, an excreta sensor, a suction device, and a rinse device;
  the bedpan is movably disposed on the pressure-sensing mattress;
  the excreta sensor is installed in the bedpan to detect the presence of excrement and output excreta detection data;
  the suction device is connected to the bedpan to suction excrement out of the bedpan;
  the rinse device is connected to the bedpan and outputs washing liquid for cleaning;
  the status feedback data of the electronic diaper machine include excreta detection data output from the excreta sensor, suction status data output from the suction device, and rinse status data from the rinse device, the CPU is connected to the excreta sensor, the suction device, and the rinse device, and the CPU receives the excreta detection data, the suction status data and the rinse status data and calculates and outputs task execution signals to drive the suction device and/or the rinse device to operate.

In an embodiment of the present invention, the system controller is in communication with a monitoring center, the monitoring center is equipped with a server and an electronic whiteboard connected to the server;
  the server is in communication with the CPU to store status feedback data received by the CPU, data obtained by the CPU or the AI deep learning module, and the task execution signals output from the CPU;
  the electronic whiteboard is connected to the server, and displays at least one monitoring display area corresponding to the current status of the electric turning bed, and the monitoring display area includes a bedridden person code, monitoring status fields, and status prompt fields.

In an embodiment of the present invention, the system controller and the monitoring center are connected to a cloud server for data transmission, communication, storage, and/or computation; the cloud server is used to store status feedback data received by the CPU, data obtained by the CPU or the AI deep learning module, and the task execution signals output from the CPU.

In an embodiment of the present invention, the AI deep learning module is connected to the cloud server to read the status feedback data of the subsystems stored in the cloud server, and synchronously feed back data of the AI recommended turning mode obtained from the operation based on the status feedback data of the subsystems to the cloud server, the system memory, and the server of the monitoring center for storage.

In an embodiment of the present invention, the system controller further includes a human-machine interface module; the human-machine interface module includes an information display area that is used to display the current status information of the bedridden person and warning information and suggestion information provided by the system controller.

In an embodiment of the present invention, the human-machine interface module includes a language switch key to switch display language of the information display area.

In an embodiment of the present invention, the system controller further includes a human-machine interface module; the human-machine interface module includes a plurality of bed frame adjustment keys, and the bed frame adjustment keys are used to adjust the amplitude of single or combined movements.

In an embodiment of the present invention, the human-machine interface module further includes a movement lock key to lock or unlock the movement of the electric turning bed.

In an embodiment of the present invention, the system controller further includes a human-machine interface module, the human-machine interface module includes an emergency operation key for automatically regulating the electric turning bed to form a state suitable for emergency operation according to the standard specifications of electrical medical equipment IEC60601-2-52 and CNS 15521.

Regarding the technology, means, and other functions adopted by the present invention to achieve the above objectives, we hereby provide preferred feasible embodiments and a detailed explanation in conjunction with the drawings as follows.

BRIEF DESCRIPTION OF THE DRAWINGS

FIGS. 6A and 6B is a schematic diagram of the present invention showing the content displayed on the electronic whiteboard display used in the monitoring center;

FIGS. 11A and 11B is the record form of the bedridden person's status output by the system controller of the present invention.

DETAILED DESCRIPTION

In the detailed description below, many specific details are elaborated to provide a thorough understanding of the present invention. However, those with ordinary knowledge in the technical field to which the present invention belongs will understand and can practice the present invention without these specific details. In other cases, there is no detailed description of well-known methods, processes, and/or components to avoid making the present invention unclear.

In order to facilitate the understanding of the present invention, the following will be explained in conjunction with embodiments.

Figure 1:
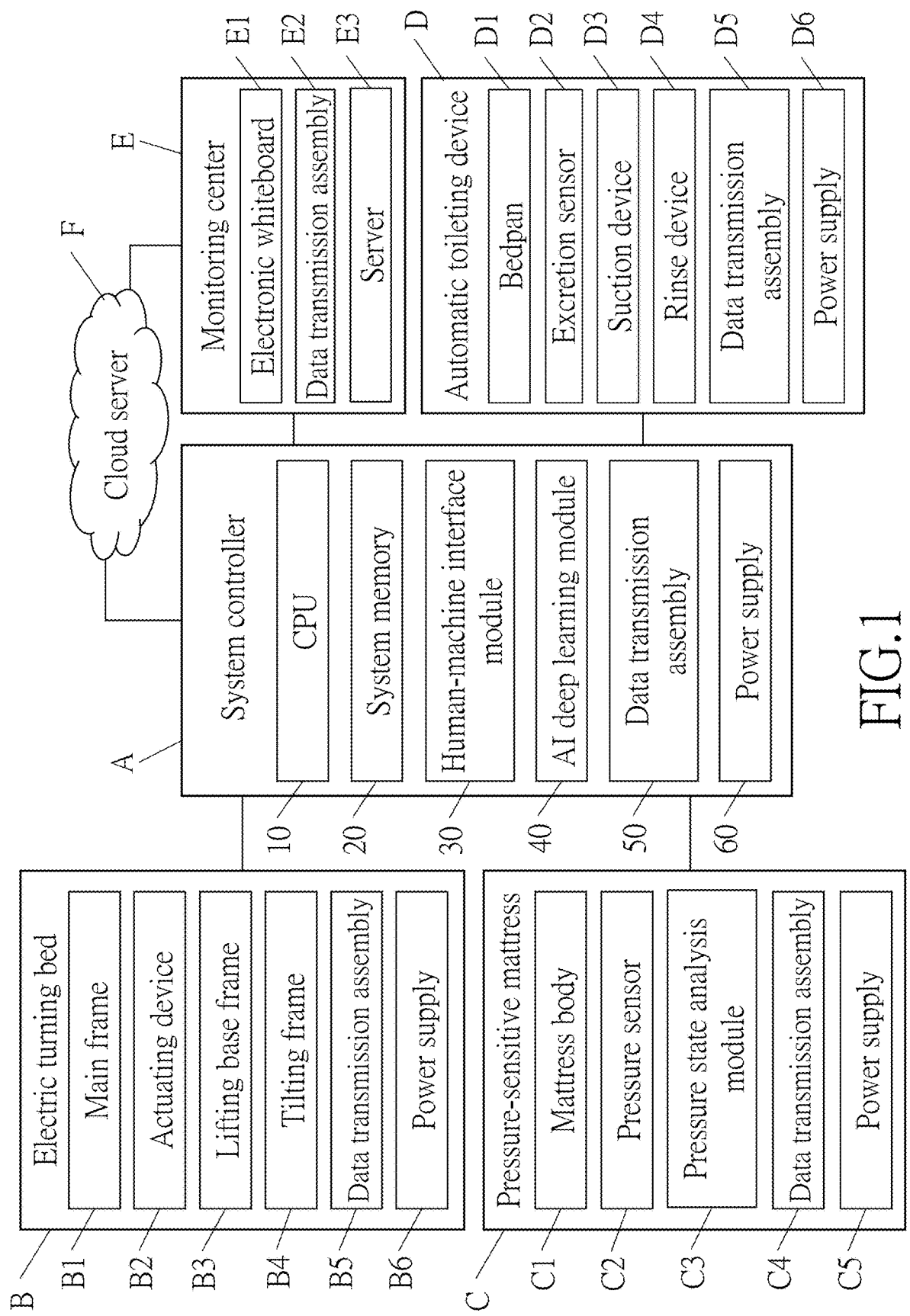
FIG. 1 is a schematic diagram of the structure of the integrated automatic turning bed system of the present invention.

As shown in FIG. 1, the integrated automatic turning bed system of the present invention includes a system controller A and a plurality of subsystems connected to it. The subsystems each include but is not limited to at least one electric turning bed B, at least one pressure-sensing mattress C, and at least one electronic diaper machine D. The system controller A is used to receive and store status feedback data from the electric turning bed B, the pressure-sensing mattress C, and the electronic diaper machine D. The system controller A sends out task execution signals to the electric turning bed B, the pressure-sensing mattress C, and the electronic diaper machine D after calculation based on the status feedback data, in order to drive these subsystems to act according to the task execution signals.

As shown in FIG. 1, the system controller A includes a CPU 10 and a plurality of functional components connected to it. These functional components include a system memory 20, a human-machine interface module 30, an AI (Artificial Intelligence) deep learning module 40, a data transmission assembly 50, and a power supply 60. Among them, the system controller A can be a control box that integrates the above functional components into an integrated shell for integrated installation on the caregiver end or integrates the above functional components into a touch control device for integrated installation on the caregiver end's care system.

Figure 2:
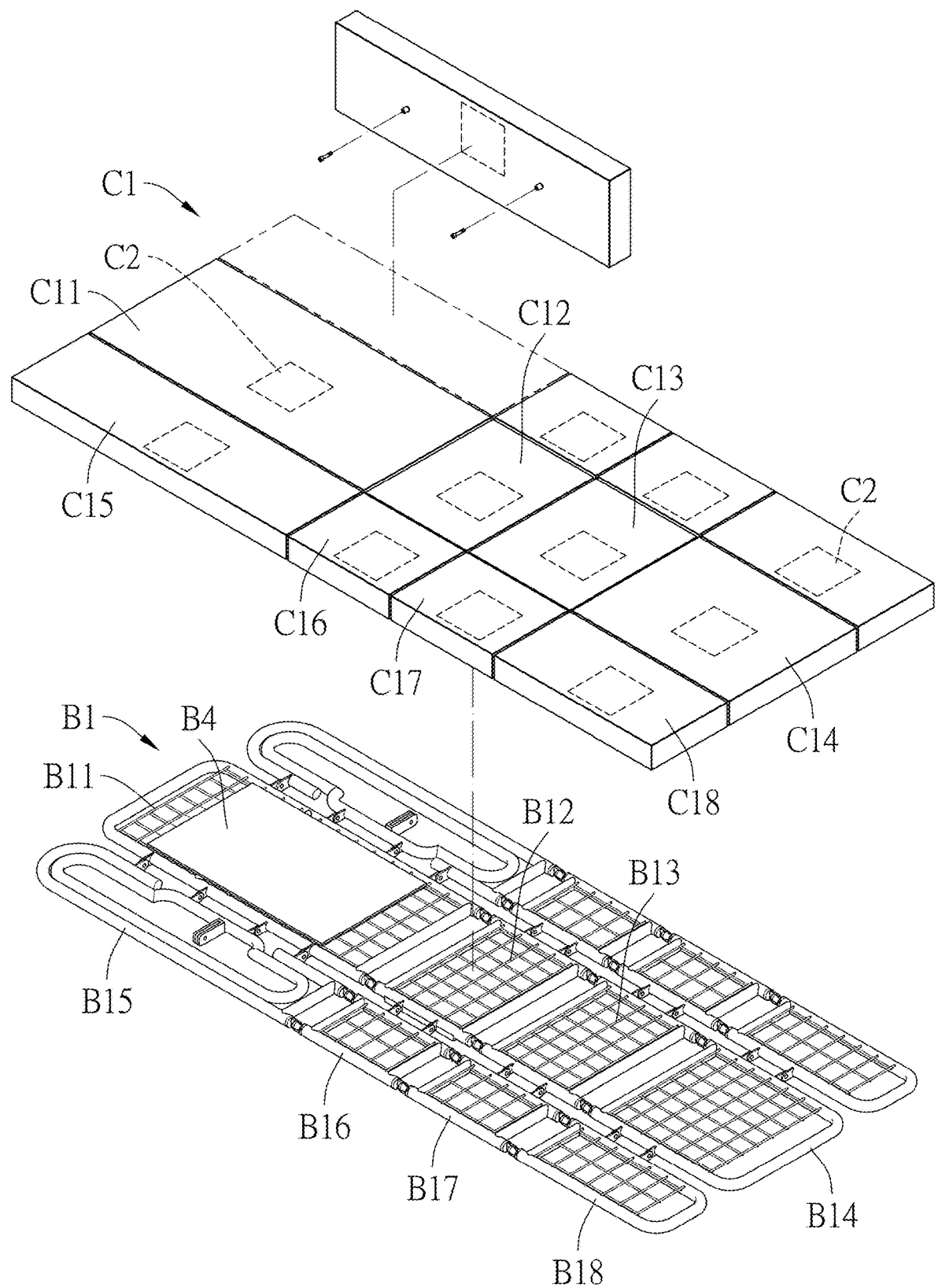
FIG. 2 is an exploded view of the main frame and the pressure-sensing mattress of the electric turning bed of the present invention.
Figure 4:
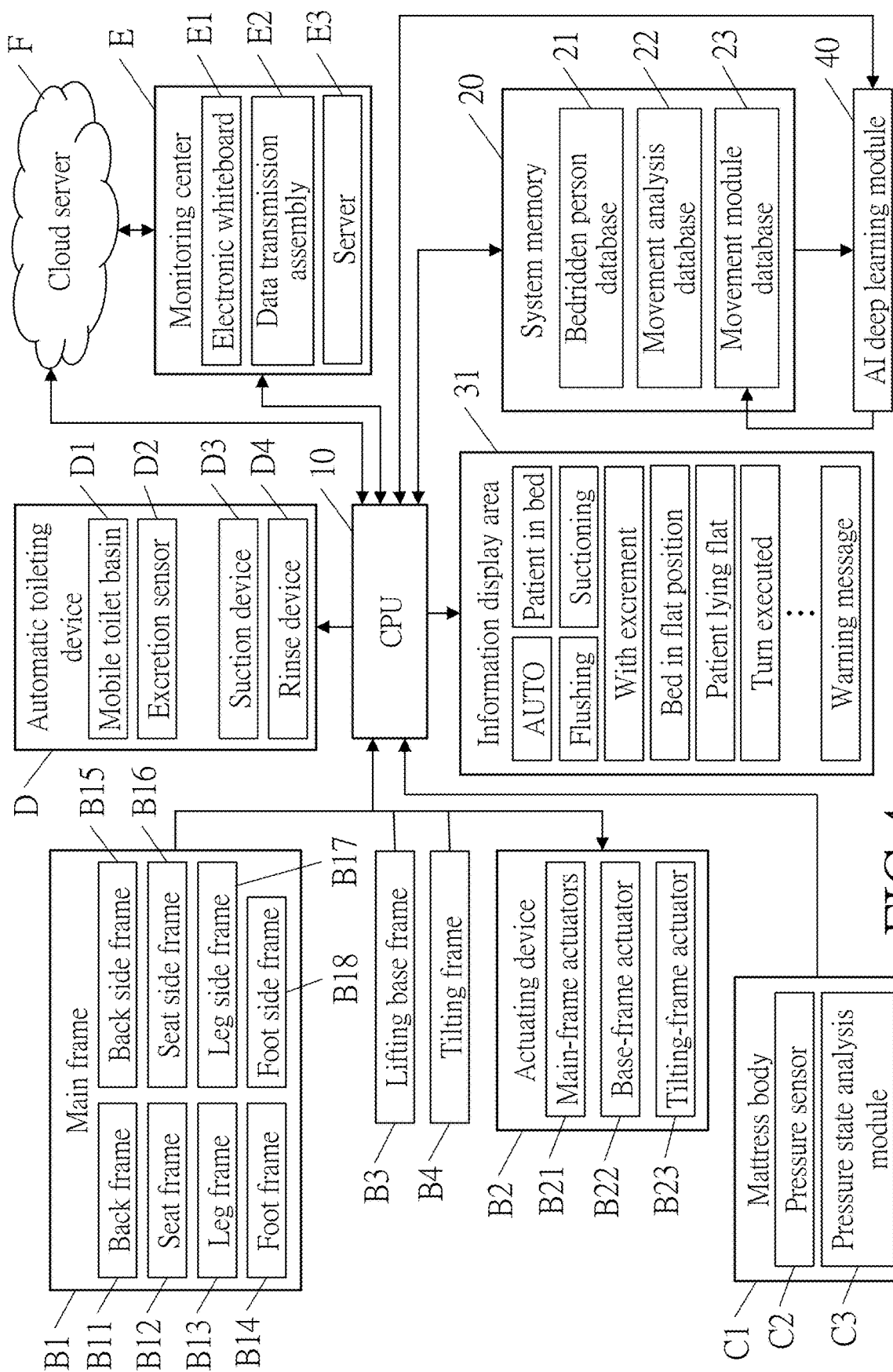
FIG. 4 is a schematic diagram of the data transmission architecture of the CPU and the system memory, the AI deep learning module, as well as the electric turning bed, the pressure-sensing mattress, and the electronic diaper machine of the present invention.

As shown in FIGS. 1, 2, and 4, the electric turning bed B includes a main frame B1, an actuating device B2, a lifting base frame B3, a tilting frame B4, a data transmission assembly B5, and a power supply B6. Among them, the main frame B1 is a foldable bed frame composed of twelve sub-frames. The actuating device B2 includes twelve main-frame actuators B21 independently connected to the twelve sub-frames, a base-frame actuator B22 independently connected to the lifting base frame B3, and a tilting-frame actuator B23 independently connected to the tilting frame B4.

Figure 3:
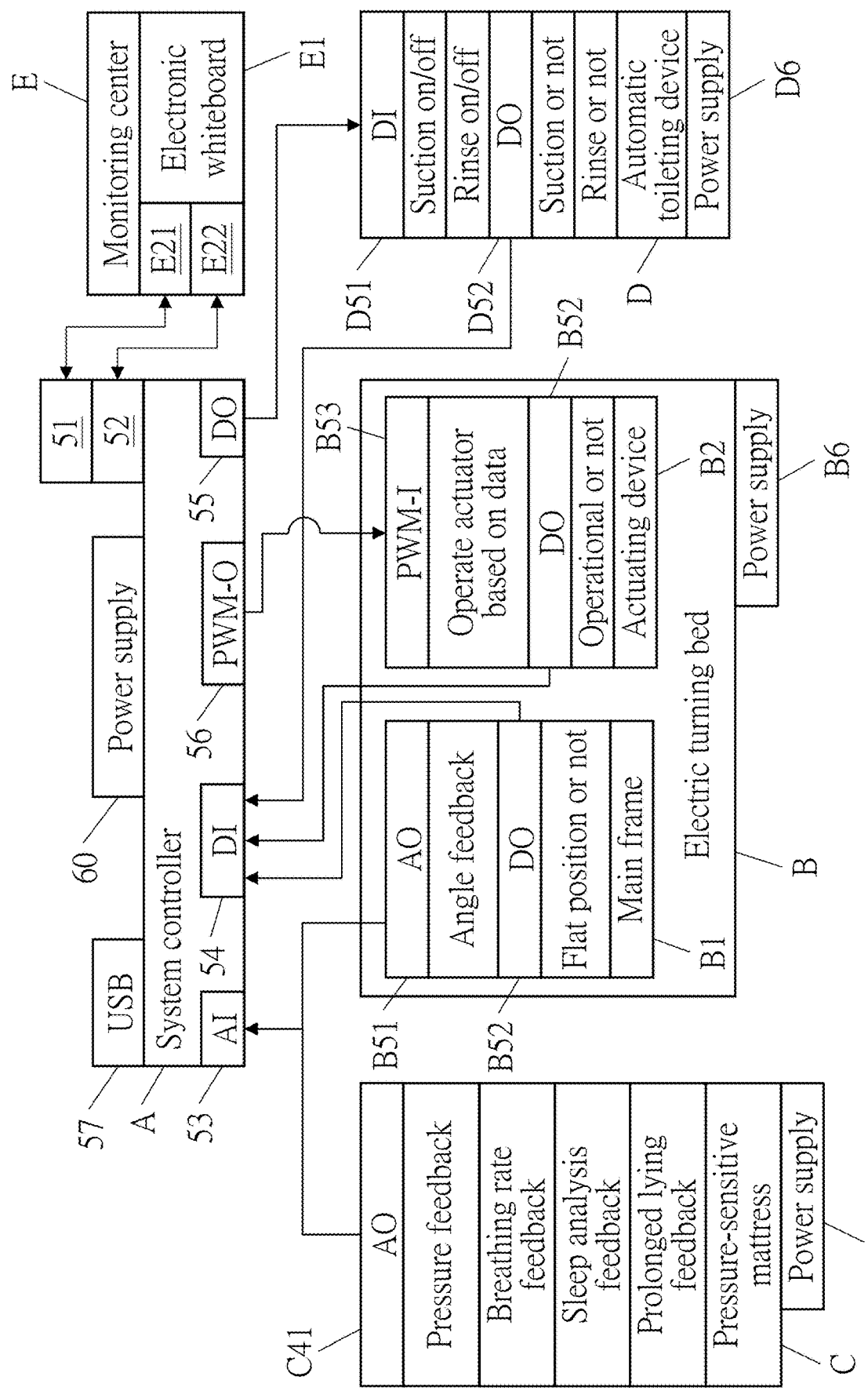
FIG. 3 is a schematic diagram of the communication and collaboration between the system controller of the present invention and the electric turning bed, the pressure-sensing mattress, and the electronic diaper machine.

As shown in FIGS. 2 and 4, the twelve sub-frames of the main frame B1 are a back frame B11, a seat frame B12, a leg frame B13, and a foot frame B14 corresponding to the respective parts of the human body, as well as two back side frames B15, two seat side frames B16, two leg side frames B17, and two foot side frames B18 disposed at two sides of the respective part-frames. As shown in FIGS. 2 to 4, the twelve main-frame actuators B21 of the actuating device B2 include a back frame actuator, a seat frame actuator, a leg frame actuator, a foot frame actuator, a back side frame actuator, a seat side frame actuator, a leg side frame actuator, and a foot side frame actuator. The twelve main-frame actuators B21 are respectively connected to the CPU 10 and independently connected to the corresponding sub-frames, and each of the main-frame actuators B21 is provided with a frame motion sensing unit, which is used to independently detect and output the status feedback data of its corresponding sub-frame. The CPU 10 is connected to the frame motion sensing units of the respective main-frame actuators B21; so that the CPU 10 receives status feedback data from the respective main-frame actuators B21 and output task execution signals to drive the main-frame actuators B21, the base-frame actuators B22, and/or the tilting-frame actuators B23 to operate, thereby driving the folding or flattening of the respective sub-frames of the main frame B1.

As shown in FIG. 2, the lifting base frame B3 is located below the main frame B1, and the base-frame actuator B22 is connected to the CPU 10 and independently connected to the lifting base frame B3. The base-frame actuator B22 is provided with a frame motion sensing unit to independently detect and output the status feedback data of the lifting base frame B3. The CPU 10 is connected to the frame motion sensing unit of the base-frame actuator B22; so that the CPU 10 receives status feedback data from the base-frame actuator B22 and outputs task execution signals to drive the base-frame actuator B22 to act, thereby driving the lifting base frame B3 to rise or fall, and adjusting the main frame B1 to an appropriate height position.

As shown in FIG. 2, the tilting frame B4 is located on the top surface of the back frame B11 of the main frame B1. The tilting-frame actuator B23 is connected to the CPU 10 and independently connected to the tilting frame B4, and the tilting-frame actuator B23 is provided with a frame motion sensing unit to independently detect and output the status feedback data of the tilting frame B4. The CPU 10 is connected to the frame motion sensing unit of the tilting-frame actuator B23; so that the CPU 10 receives status feedback data from the tilting-frame actuator B23 and outputs task execution signals to drive the tilting-frame actuator B23 to operate, thereby driving the tilting frame B4 to slightly lift or reset, causing the head of the bedridden person to tilt up by about 15 degrees, to facilitate the bedridden person to eat and reduce the occurrence of foreign body choking (that is choking) during bedridden eating.

In the embodiment of the present invention, the respective frame motion sensing units disposed on the main frame B1 or the actuating device B2 are independently connected to the data transmission assembly B5 to transmit the detected status feedback data to the system controller A through the data transmission assembly B5. The aforementioned frame motion sensing units can be independently installed on the main-frame actuators B21, the base-frame actuators B22, and the tilting-frame actuators B23, or the frame motion sensing units can be independently installed on the twelve sub-frames of the main frame B1 to detect the displacement distance and/or displacement angle of the respective sub-frames, or, the aforementioned frame motion sensing units can be simultaneously installed on the actuating device B2 and the twelve sub-frames to more accurately detect the motion status of the main frame B1. Specifically, the aforementioned frame motion sensing units can be selected from but not limited to angle sensors (such as gyroscopes), Hall effect sensors, telescopic displacement sensors, and/or resistive bending sensors. The aforementioned angle sensors (such as gyroscopes), Hall effect sensors, and telescopic displacement sensors can be installed at or near the pivot points of the twelve sub-frames of the main frame B1 to detect the motion status. The aforementioned resistive bending sensors can be installed on the surface or inside of the twelve sub-frames of the main frame B1 to detect the motion status.

In the embodiment of the present invention, the status feedback data output by the respective main-frame actuators B21 includes displacement distance data and/or displacement angle data of the twelve sub-frames of the main frame B1. The status feedback data output by the base-frame actuators B22 includes displacement distance data and/or displacement angle data of the lifting base frame B3. The status feedback data output by the tilting-frame actuators B23 includes displacement distance data and/or displacement angle data of the tilting frame B4. In this way, the CPU 10 outputs task execution signals that drive the main frame B1, the lifting base frame B3, and/or the tilting frame B4 to operate based on the displacement distance data and/or the displacement angle data.

In the embodiments of the present invention, the electric turning bed B used in the present invention may include, but is not limited to, the hospital bed provided by the Taiwan Patent No. 1297266.

According to the above, in the embodiment of the present invention, the electric turning bed B can drive the bedridden person to perform the following movements:

(1) The first movement is to raise or lower the bedridden person. It drives the lifting and lowering of the lifting base frame B3 through the base-frame actuator B22, which consequently drives the main frame B1 to complete the lifting or lowering movement.

(2) The second movement: lift or lower the back of the bedridden person. The main-frame actuator B21 drives the back frame B11 to complete the lifting and lowering movement.

(3) The third movement: lift or lower the feet of the bedridden person. The third movement is achieved by driving the connection between the leg frame B13 and the foot frame B14 up or down through the main-frame actuator B21.

(4) The fourth movement: Make the bedridden person flip to the right or left as a whole. The main-frame actuator B21 drives the back side frame B15, the seat side frame B16, the leg side frame B17, and the foot side frame B18 on one side thereof to fold up, while the back side frame B15, the seat side frame B16, the leg side frame B17, and the foot side frame B18 on the other side thereof are driven to fold down together, thereby driving the back frame B11, the seat frame B12, the leg frame B13, and the foot frame B14 to flip to the left or right, that is, the part-frames in the middle are lifted on the side where the side frames fold down, making the four part-frames in the middle form a state of one side high and one side low to achieve the fourth movement.

(5) The fifth movement: Raise the back of the bedridden person slightly or reset. The tilting-frame actuator B23 drives the tilting frame B4 to complete a small amplitude lifting movement or resetting.

As shown in FIG. 1, the pressure-sensing mattress C includes a mattress body C1, pressure sensors C2, a pressure state analysis module C3, a data transmission assembly C4, and a power supply C5.

As shown in FIG. 2, the mattress body C1 is a foldable mattress composed of twelve cushions corresponding to the twelve sub-frames that bear the main frame B1. The twelve cushions include a back cushion C11, a seat cushion C12, a leg cushion C13, and a foot cushion C14, as well as a back side cushion C15, a seat side cushion C16, a leg side cushion C17, and a foot side cushion C18 located on two sides of the respective cushions. The aforementioned twelve cushions are in an independent and separate state; so that the cushions of the pressure-sensing mattress C do not interfere with each other during the folding process, nor do they interfere with the folding movement of the main frame B1. The respective cushions can be fixed to the corresponding sub-frames of the main frame B1 by screws.

As shown in FIG. 2, inside each of the twelve cushions of the mattress body C1 are all provided pressure sensors C2 (including back pressure sensor, seat pressure sensor, leg pressure sensor, foot pressure sensor, back side pressure sensor, seat side pressure sensor, leg side pressure sensor, and foot side pressure sensor). The pressure sensing members C2 are connected to the CPU 10, respectively, to independently detect and output the status feedback data of the corresponding cushions; so that the status feedback data from the respective pressure sensors C2 include the pressure sensing data of the twelve cushions. By doing so, the CPU 10 can receive pressure sensing data from the respective pressure sensors C2 and obtain the biometric data of the bedridden person. Based on the biometric data, the CPU 10 outputs task execution signals that drive the main frame B1, the lifting base frame B3, and/or the tilting frame B4 to operate.

In the embodiment of the present invention, the pressure state analysis module C3 is connected to the respective pressure sensors C2, and the pressure state analysis module C3 does calculations based on the pressure sensing data output by the respective pressure sensors C2 to obtain and output the biometric data of the bedridden person. The CPU 10 receives and outputs task execution signals that drive the main frame B1, the lifting base frame B3, and/or the tilting frame B4 to operate based on the biometric data. Therefore, the pressure-sensing mattress C can optionally be provided with the pressure state analysis module C3, and when provided with the pressure state analysis module C3, it can do calculation of the biometric data of the bedridden person to reduce the workload of the CPU 10.

In the embodiment of the present invention, the pressure value refers to the pressure sensing data of the twelve cushions of the pressure-sensing mattress C. Respiratory frequency, heartbeat frequency, sleep analysis, and long lying analysis are calculated based on the changes in the aforementioned pressure sensing data caused by the bedridden person during breathing, heartbeat, sleep state, and long lying state.

In the embodiments of the present invention, the pressure-sensing mattress C used in the present invention may include, but is not limited to, the multi-piece mattress for a rollaway bed frame provided in the Taiwan patent publication No. M621079.

As shown in FIG. 1, the electronic diaper machine D includes a bedpan D1, an excreta sensor D2, a suction device D3, a rinse device D4, a data transmission assembly D5, and a power supply D6. Among them, the bedpan D1 is movable and can be placed on the pressure-sensing mattress C during use and removed after use. The excreta sensor D2 is installed in the bedpan D1 to detect the presence of foreign objects and output an excreta detection data. The excreta sensor D2 can obtain the excreta detection data through pressure sensing technology. The suction device D3 is provided with a suction pipeline connected to the bedpan D1, which is used to suction out excrement entering the bedpan D1. The rinse device D4 is connected to the bedpan D1 by a pressurized water outlet pipeline, which is used to output the washing liquid to the bedpan D1 and clean the bedridden person. During cleaning, dirt falls into the bedpan D1 and is immediately sucked out by the suction device D3.

Based on this, as shown in FIGS. 1 and 4, the status feedback data of the electronic diaper machine D includes the excreta detection data (with or without foreign objects) output by the excreta sensor D2, the suction status data (in suction, off suction) output by the suction device D3, and the rinse status data (in water washing, off water washing) output by the rinse device D4; so that the CPU 10 is connected to the excreta sensor D2, the suction device D3 and the rinse device D4, and the CPU 10 receives the excreta detection data, the suction status data, and the rinse status data, and outputs task execution signals that drive the suction device D3 and/or the rinse device D4 to operate based on these data.

In the embodiments of the present invention, the aforementioned system controller A, the electric turning bed B, the pressure-sensing mattress C, and the electronic diaper machine D can be selectively set for use in the home of a single bedridden person, or can also be set for use in care units, such as nursing institutions or hospitals that provide care services for bedridden people.

As shown in FIG. 1, when the current system controller A and its subsystems (the electric turning bed B, the pressure-sensing mattress C, and/or the electronic diaper machine D) are used in the care unit, the system controller A and its subsystems can monitor and care for multiple bedridden people in real-time and simultaneously by setting a monitoring center E in the care unit, and respond to changes in the bedridden person's status in a timely manner, as well as selectively feedback the bedridden person's status to their family members. In the embodiment of the present invention, as shown in FIG. 1, the monitoring center E is provided with a server E3, an electronic whiteboard E1 and a data transmission assembly E2 which are connected to the server E3.

As shown in FIG. 3, the server E3 performs data transmission/communication with the data transmission assembly 50 of the system controller A through the data transmission assembly E2. The server E3 can serve as a backup local storage system for the system controller A to store the status feedback data received by the CPU 10, the data obtained by the CPU 10 or the AI deep learning module 40 through operation, and the task execution signal and other data output by the CPU 10.

In the embodiment of the present invention, the system controller A and the monitoring center E can also be connected to a cloud server F to perform the aforementioned data storage and/or data computation. The cloud server F can serve as a remote storage system for the system controller A and the server E3, and can further allow family members of bedridden people to obtain specific bedridden person's care information and current status by use of connected devices or smart devices connected to the cloud server F through the Internet of Things. Among them, the connected devices and the smart devices may include but are not limited to devices such as smartphones, personal computers (PCs), laptops, tablets, workstations, embedded systems (such as in car computers), etc.

In addition, the AI deep learning module 40 of the system controller A can also communicate with the cloud server F to read the status feedback data of the subsystems stored in the cloud server F, and synchronously feed back the results (such as AI recommended turning mode) obtained from the operation based on the status feedback data of the subsystems to the cloud server F, the system memory 20, and the server E3 of the monitoring center E for storage.

As shown in FIGS. 6A and 6B, the electronic whiteboard E1 displays the monitoring display areas corresponding to the current status of the respective electric turning beds B. Each of the monitoring display areas includes a bedridden person code (such as the 1st bed), the monitoring status fields (such as executing commands to be executed by subsystems such as turning over, no excrement or urine, patient in bed, and presenting monitoring results of the subsystem on the bedridden person), and status prompt fields (such as prompts for the movements or monitoring results being performed by the subsystem on the bedridden person during the first turning over, patient off bed, and suction). In the embodiment of the present invention, the electronic whiteboard E1 can be an electronic whiteboard, a display of a tablet computer, or a display of the servo device itself, in a care unit.

In the embodiment of the present invention, the data transmission assembly 50/B5/C4/D5 used in the system controller A, the electric turning bed B, the pressure-sensing mattress C, and the electronic diaper machine D may include, but are not limited to, analog interface, digital interface, and pulse width modulation interface (PWM). In FIG. 3, the output end of the analog interface is abbreviated as AO (Analog Output), and the input end is abbreviated as AI (Analog Input). The output end of the digital interface is abbreviated as DO (Digital Output), and the input end is abbreviated as DI (Digital Input). The output end of the pulse width modulation interface is abbreviated as PWM-O (PWM Output), and the input end is abbreviated as PWM-I (PWM Input).

In the embodiment of the present invention, as shown in FIG. 3, the data transmission assembly 50 of the system controller A includes a wired transmission module 51, a wireless transmission module 52, an analog interface input 53, a digital interface input 54, a digital interface output 55, a PWM interface output 56, and a USB connector 57, which are connected to the CPU 10. Among them, the wired transmission module 51 can achieve wired transmission/communication of data through network cable connection. The wireless transmission module 52 can achieve wireless data transmission/communication through WiFi technology connection. The analog interface input 53 is used to receive data from the subsystem's analog interface output. The digital interface input 54 is used to receive data from the subsystem's digital interface output. The digital interface output 55 is used to output commands to the digital interface input of the subsystem. The PWM interface output 56 is used to output commands to the PWM interface input of the subsystem. The USB connector 57 is used to connect to a USB storage device or USB transmission device.

As shown in FIG. 3, in the embodiment of the present invention, the main frame B1 of the electric turning bed B is provided with an analog interface output B51 and a digital interface output B52 for data transmission/communication with the analog interface input 53 and the digital interface input 54 of the system controller A. For example, the main frame B1, through its analog interface output B51, feeds back the angle value of the current sub-frame measured by its frame motion sensing unit to the system controller A through the analog interface input 53. For example, the main frame B1, through its digital interface output B52, feeds back the status whether the bed surface is lying flat or not to the system controller A.

As shown in FIG. 3, in the embodiment of the present invention, the actuating device B2 of the electric turning bed B is additionally provided with a PWM interface input B53 and a digital interface output B52 for data transmission/communication with the PWM interface output 56 and the digital interface input 54 of the system controller A. For example, the actuating device B2 receives a task execution signal output from the PWM interface output 56 of the system controller A through the PWM interface input B53, in order to drive a specific actuator based on the data carried by the task execution signal. For example, the actuating device B2 feeds back the operating status of the actuating device B2 to the system controller A through its digital interface output B52 and the digital interface input 54.

As shown in FIG. 3, in the embodiment of the present invention, the pressure-sensing mattress C is provided with an analog interface output C41 for data transmission/communication with the analog interface input 53 of the system controller A. For example, the pressure-sensing mattress C, through its analog interface output C41, feeds back the pressure value, respiratory frequency, sleep analysis, and long lying analysis data obtained by the pressure state analysis module C3 to the system controller A through the analog interface input 53.

As shown in FIG. 3, in the embodiment of the present invention, the electronic diaper machine D is provided with a digital interface input D51 and a digital interface output D52 for data transmission/communication with the digital interface output 55 and the digital interface input 54 of the system controller A. For example, the electronic diaper machine D feeds back the status data of the suction device D3 and the rinse device D4 through its digital interface output D52 to the system controller A through the digital interface input 54. For example, the electronic diaper machine D receives a task execution signal output from the digital interface output 55 of the system controller A through its digital interface input D51 to drive the suction device D3 and/or the rinse device D4 to turn on or off based on the data carried by the task execution signal.

As shown in FIG. 3, in the embodiment of the present invention, the monitoring center E is provided with a wired transmission module E21 and a wireless transmission module E22 for data transmission/communication with the wired transmission module 51 and the wireless transmission module 52 of the system controller A.

Specifically, in the embodiment of the present invention, the power supply 60 of the system controller A, the power supply B6 of the electric turning bed B, the power supply C5 of the pressure-sensing mattress C, and the power supply D6 of the electronic diaper machine D refer to the components used to provide necessary electrical energy for their motor devices. The aforementioned power supply can be a transformer or power switch connected to a DC or AC power source, or a rechargeable battery.

The above explains the specific composition of the system controller A and the various subsystems (the electric turning bed B, the pressure-sensing mattress C, the electronic diaper machine D). The following describes the collaborative relationship between the system controller A and various subsystems and the operational logic of the integrated automatic turning bed system of the present invention.

As shown in FIG. 4, the system memory 20 of the system controller A is provided with a bedridden person database 21, a movement analysis database 22, and a movement module database 23. The bedridden person database 21 is used to record the identity information, medical records, care modes (including turning mode), and other data related to bedridden people. The movement analysis database 22 is used to record and store data (such as date, time, current state of the integrated automatic turning bed system, whether the electric turning bed is in automatic turning mode, current state of the bedridden person, whether there is excrement, whether flushing is started, whether suction is started, whether the bedridden person is in bed, etc) related to the bedridden person's status obtained from the system controller A's analysis based on the status feedback data, for outputting the bedridden person status record table shown in FIGS. 11A and 11B. The movement module database 23 is used to record and store: (1) the system's built-in "default turning mode", (2) the caregiver's "adjusted turning mode" based on the preset turning mode, (3) "manual control turning mode" manually input by the caregiver based on the specific bedridden person's state, (4) "AI recommended turning mode" output by the AI deep learning system, and (5) caregiver's "AI adjusted tuning mode" based on the recommended turning mode.

Figure 5:
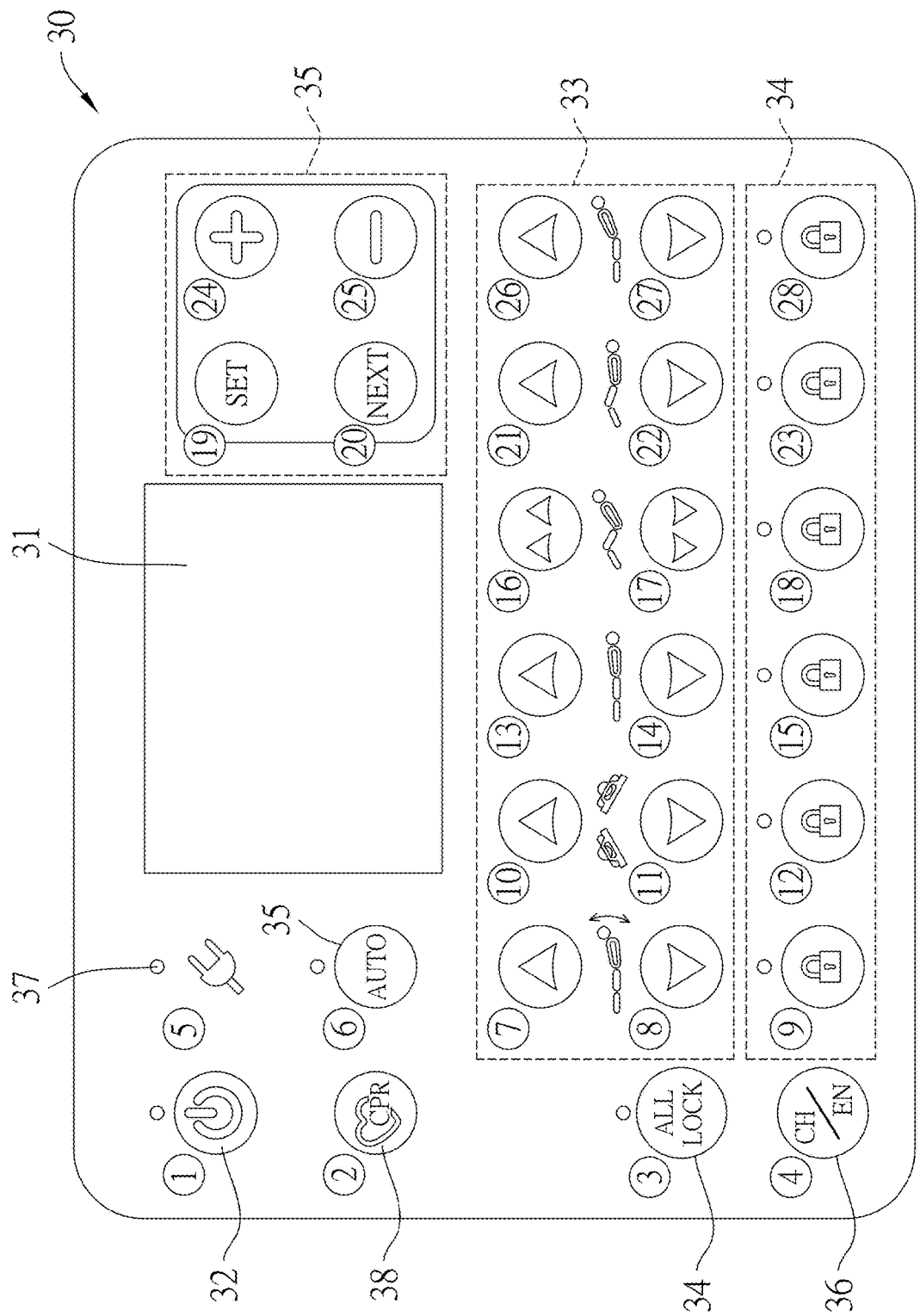
FIG. 5 is a schematic diagram of the operation interface of the human-machine interface module of the present invention.

As shown in FIG. 5, the human-machine interface module 30 of the system controller A includes an information display area 31, a power indicator light 37, and various control keys. These control keys include a power toggle key 32, bed frame adjustment keys 33, a movement lock key 34, auto-control setting keys 35, an language switch key 36, and an emergency operation key 38. In one embodiment of the present invention, when the system controller A is in the form of a control box, the human-machine interface module 30 can achieve the purpose of inputting task execution signals to the system controller A by materializing the abovementioned control keys and connecting the control keys to the CPU 10 via a printed circuit board (PCB) for the caregiver to operate. In another embodiment of the present invention, when the system controller A is in the form of a touch device, the human-machine interface module 30 can simulate the above control keys on a touch panel device for the caregiver to operate, achieving the purpose of inputting task execution signals to the system controller A.

As shown in FIGS. 4 and 5, the information display area 31 is used to display the current status information of the bedridden person (such as date, time, current status of the integrated automatic turning bed system, whether the electric turning bed is in automatic turning mode, current status of the bedridden person, whether there is excrement, whether flushing is started, whether suction is started, whether the bedridden person is on the bed, etc.), warning information and suggestion information provided by the system controller A. The content displayed in the information display area 31 is not limited to the above, and can be increased or decreased according to the settings of the system controller A to provide information that is beneficial for caring for the bedridden person.

As shown in FIG. 5, the power toggle key 32 of the human-machine interface module 30 is used to control the operation of the CPU 10 of the system controller A to start or stop data detection, recording, calculation, and transmission. As indicted by the circled numerals in FIG. 5, the bed frame adjustment key(s) 33 and the movement lock key 34 of the human-machine interface module 30 can be set according to single movement control and combined movements control. Each single movement or combination of movements has two bed frame adjustment keys 33 indicating an increase (A) or decrease (V) in the amplitude of the movement, respectively, for adjustment, and is matched with one movement lock key 34 to lock or unlock the movement of the electric turning bed B.

Specifically, as shown in FIG. 5, the single movement control key can include but not be limited to: (1) a set of keys indicated by the circled numerals 13/14, which are used to drive the main frame B1 to lift or lower to achieve the first movement of the bedridden person, and the corresponding movement lock key 34 is the key with the circled numeral 15. (2) The set of keys with the circled numerals 26/27 are used to drive the back frame B11 to lift or lower to achieve the second movement of the bedridden person, and the corresponding movement lock key 34 is the key with the circled numeral 28. (3) The set of keys with the circled numerals 21/22 are used to drive the leg frame B13 and the foot frame B14 to lift or lower to achieve the third movement of the bedridden person, and the corresponding movement lock key 34 is the key with the circled numeral 23. And, (4) the set of keys with the circled numerals 10/11 are used to drive the main frame B1 to turn right or left to achieve the fourth movement of the bedridden person, and its corresponding movement lock key 34 is the key with the circled numeral 12.

Specifically, as shown in FIG. 5, the combined movement control key can include but is not limited to: (1) a set of keys with the circled numeral 7/8, which are used to drive the main frame B1 to turn to the right or left and fix it at any angle, then, the tilting frame B4 is slightly raised or reset to achieve the combination of the fourth and fifth movements of the bedridden person, and the corresponding movement lock key 34 is the key with the circled numeral 9. (2) The set of keys with the circled numeral 16/17 are used to drive the back frame B11 and the leg frame B13 to be raised or lowered simultaneously, in order to achieve the combination of the second and third movements of the bedridden person, and the corresponding movement lock key 34 is the key with the circled numeral 18.

In the embodiment of the present invention, when the single movement control key and the combined movement control key drive the corresponding sub-frames of the main frame B1 to operate, the CPU 10 continuously controls the corresponding sub-frames to operate based on the commands generated by the control keys being continuously pressed. And the system controller A compares the activity amplitude data of the respective sub-frames with the status feedback data from the electric turning bed B, and stops driving when the sub-frames are driven to move to the maximum or minimum value of the activity amplitude data. In addition, when the driven sub-frames do not reach the maximum or minimum value of its activity amplitude data, the CPU 10 stops driving the sub-frames to move by stopping outputting commands by the control keys, thereby achieving the adjustment of the sub-frames. Among them, the activity amplitude data of the respective sub-frames mentioned above can also include other logic (parameters) to limit the movement amplitude of the sub-frames. Furthermore, when considering the issue of mechanism interference during different movements of the electric turning bed B, when the CPU 10 determines that the current state of the main frame B1 cannot be directly driven to move by the command output by the control keys based on the status feedback data and built-in logic of the electric turning bed B, the CPU 10 first drives the main frame B1 to return to the lying state, then execute the command output by the control keys to drive the corresponding sub-frames to move.

Specifically, taking the combination control of the fourth and fifth movements as an example, when the tilting frame B4 is raised to the maximum angle limit (such as lifting by 15°), the CPU 10 will automatically stop the movement. When the control key is released during the process of lifting the tilting frame B4 from 0° to less than 15°, it will cause the tilting frame B4 to stay at the current lifting angle.

Specifically, in addition to the maximum and minimum values of the aforementioned activity amplitude data, the limitation of the activity amplitude of the sub-frames is illustrated by the combination control of the second and third movements, when the back frame B11 is raised simultaneously with the leg frame B13 and the foot frame B14, the angle between the back frame B11 and the seat frame B12, as well as the angle between the leg frame B13 and the foot frame B14, must be greater than 90° to comply with the standard specifications of electrical and medical equipment, avoiding crushing and injuring the bedridden person.

Specifically, taking the combination control of the fourth and fifth movements as an example, when the tilting frame B4 needs to be lowered and reset, considering the issue of mechanism interference between the sub-frames of the main frame B1, the CPU 10 can add that when receiving a command to drive the tilting frame B4 to lower and reset, the CPU 10 first determines whether the main frame B1 is laid flat and executes the command to lay the main frame B1 flat when it is not laid flat, and then executes the command to lower and rest the tilting frame B4 again. Also, taking the single movement control of the fourth movement as an example, when the current main frame B1 is in the raised state of the back frame B11 and/or the leg frame B13 and foot frame B14, the CPU 10 will first return the main frame B1 to the lying flat state based on the status feedback data and built-in logic of the main frame B1 after receiving the turn left or right command output by pressing the control keys, then drive the main frame B1 to turn to the left or right.

Through this, the caregiver can lock the movement of the electric turning bed B by pressing the corresponding movement lock key 34 once after using the bed frame adjustment key(s) 33, and cannot operate it arbitrarily. And by pressing the same movement lock key 34 twice, the electric turning bed B is unlocked, and is returned to an operable state. In addition, the human-machine interface module 30 can also be provided with an all-locking movement lock key 34 (circled numeral 3) which can lock all movements at once, allowing caregivers to lock all movements at once by pressing the all-locking movement lock key 34 once after completing the required electric turning bed B movement setting. Moreover, by pressing one of the aforementioned bed frame adjustment keys 33, the corresponding movement locking can be released for operation.

As shown in FIG. 5, the auto-control setting keys 35 of the human-machine interface module 30 can include a SET key (the circled numeral 19), a NEXT key (circled numeral 20), a + key (circled numeral 24), a − key (circled numeral 25), and an AUTO key (circled numeral 6). The auto-control setting keys 35 are used to set the time (duration of the movement, preset automatic start/end time point) for the CPU 10 to perform a turning over movement, as well as to set the overall date and time for the system controller A. Among them, the NEXT key is used to repeatedly press to jump between multiple options for selection. The SET key is used to confirm the option and enter the option page. The + key and the − key are used to adjust the numerical values of parameters, such as the increase or decrease of date/time numerals and the increase or decrease of time length.

In one embodiment of the present invention, taking Setting Auto Turn as an example, the following describes the operation steps of using these auto-control setting keys 35 to enable the system controller A to enter automatic turning mode from manual operation mode and then return to manual operation mode:

Step (1): Pressing the SET key for 3 seconds to enter the setting mode of CPU 10. At this point, the information display area 31 displays a Select Setting page, and an option 1: Setting Auto Turn, and an option 2: Setting Date and Time.

Step (2): Use the NEXT key to jump to option 1, and use the SET key to confirm the option to enter the setting page for setting auto turn, and then it will display: Parameter 1: Total Time for all auto turn, Parameter 2: duration for Right Turn, Parameter 3: Right Angle, Parameter 4: duration for Left Turn, Parameter 5: Left Angle, and parameter 6: duration for Flat Turn (lying flat). Use the NEXT key to jump between options 1-1 and options 1-6, and use the + key and the − key to set the duration (minutes) or angle for each option.

Step (3): After all settings are completed, if there is no need to store the auto turn parameter values input in step (2), press the ALL LOCK key (circled numeral 3) of the movement lock key 34 to cause the CPU 10 to perform tasks such as not storing the aforementioned parameter values and exiting the setting mode. If storage is required, press the SET key to enable the CPU 10 to perform tasks such as storing the aforementioned parameter values, outputting commands based on the aforementioned parameter values, and exiting the setting mode.

Step (4): Press the AUTO key for 3 seconds to drive the main frame B1 to execute the setting results of steps (2) and (3). At this point, if the main frame B1 is not in a lying flat state, the CPU 10 will first execute to the task to make the main frame B1 automatically return to a lying flat state, and then drive the main frame B1 to perform an auto turn task based on the aforementioned parameter value setting results. If the main frame B1 is already in a lying flat state, the CPU 10 will drive the main frame B1 to perform an auto turn task based on the aforementioned parameter value setting results after driving the AUTO key to light up.

Step (5): During the execution of the auto turn task in step (4), if the auto turn task needs to be interrupted, the AUTO key can be pressed at any time during the process, and the CPU 10 will return to the manual operation mode after driving the AUTO key light to turn off.

As shown in FIG. 5, the emergency operation key 38 (circled numeral 2) of the human-machine interface module 30 is used to realize that when the bedridden person needs emergency rescue, the emergency operation key 38 can be pressed for 3 seconds to quickly restore the electric turning bed B from any movement state to a suitable movement state for rescue. In the embodiment of the present invention, the state of the electric turning bed B suitable for rescue is that the main frame B1 is in a horizontal state and located at the lowest height position, so as to facilitate medical personnel to take emergency measures for the bedridden person. Preferably, the electric turning bed B is set according to the standard specifications of electrical medical equipment IEC60601-2-52 and CNS 15521 to determine the movement status of the electric turning bed B during rescue.

As shown in FIG. 5, the language switch key 36 of the human-machine interface module 30 is used to switch the display language of the information display area 31; so that caregivers using different languages can quickly and easily have a consistent understanding of the state of the bedridden person, in order to provide consistent care services for the bedridden person. For example, general caregivers using Chinese and foreign caregivers using English.

As shown in FIG. 5, the power indicator light 37 of the human-machine interface module 30 is used to display the power status of the system controller A, to ensure continuous monitoring of the bedridden person's status through subsystems such as electric turning bed B, pressure-sensing mattress C, and electronic diaper machine D, ensuring the quality of care.

As shown in FIG. 4, the AI deep learning module 40 of the system controller A is used to read data from various databases in the system memory 20, analyze and learn, and ultimately output the AI modified tuning mode that is most suitable for the current needs of the specific bedridden person, for automatic correction of the caregiver's input values, or to prompt the caregiver for a more suitable turning mode, so as to avoid the care errors caused by the replacement of the caregiver, so as to avoid the care errors caused by the replacement of the caregiver.

Please refer to FIGS. 7 to 10 to illustrate the control logic of the system controller A and the respective subsystems.

Figure 7:
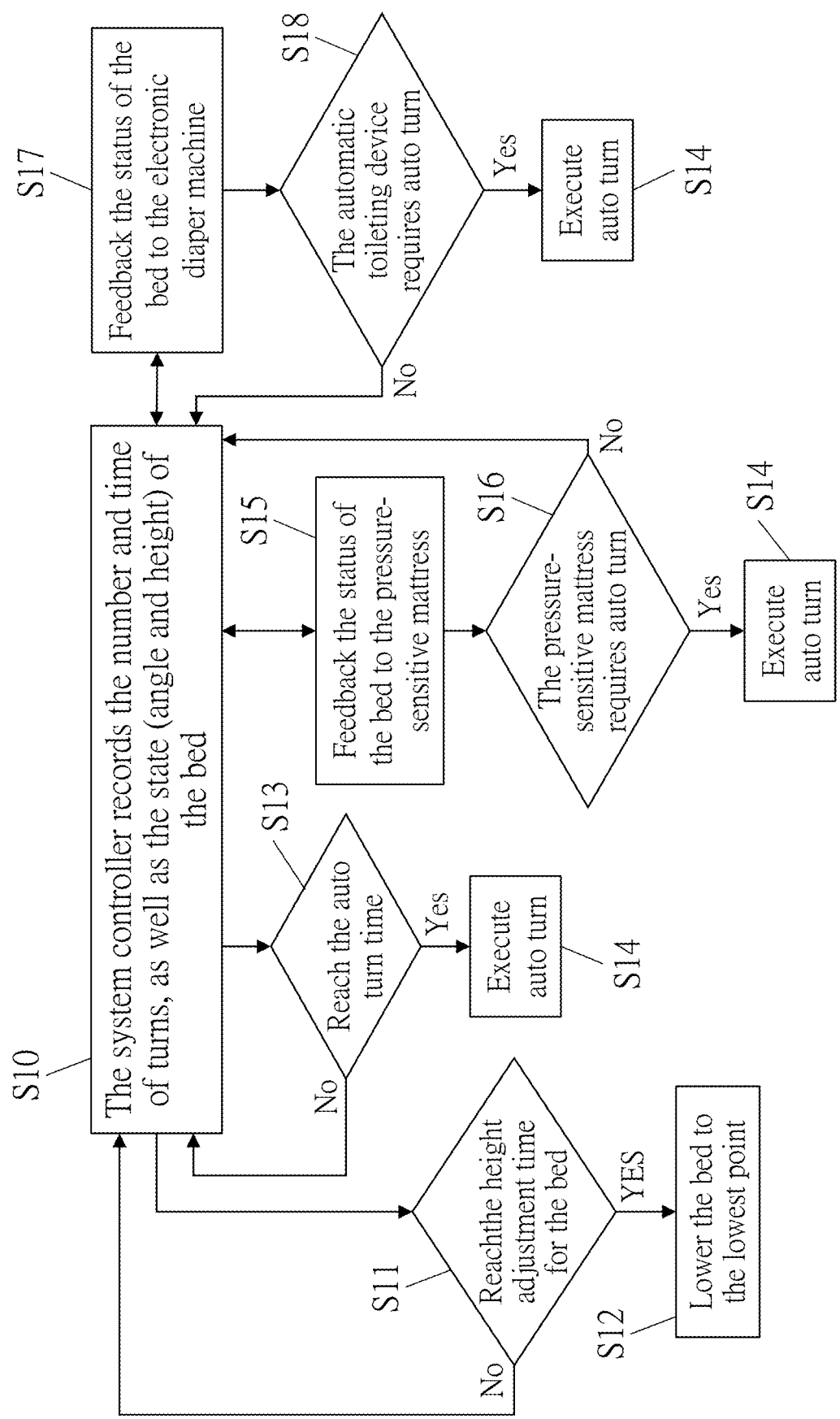
FIG. 7 is a logical schematic diagram of the system controller of the present invention controlling the electric turning bed to execute movements.

As shown in FIG. 7, the control logic of the system controller A controlling the electric turning bed B to execute movements is displayed. In step S10, the system controller A continuously receives status feedback data and obtains, by calculation, the number and time of turns, as well as the state (angle and height) of the electric turning bed B. Next, in step S11, the system controller A determines whether the height and adjustment time for the electric turning bed B have been reached based on the results obtained in step S10. When reached, the system controller A outputs a task execution signal to the electric turning bed B to execute step S12, causing the electric turning bed B to lower to the lowest point. When not reached, return to step S10.

In step S13, the system controller A determines whether the automatic turning time has been reached based on the results obtained in step S10. When the time is reached, the system controller A outputs a task execution signal to the electric turning bed B to execute step S14, causing the electric turning bed B to perform auto turn (including restoring the bedridden person to lie flat or the aforementioned second to fifth movements). When it is not reached, return to step S10.

In step S15, the system controller A receives status feedback data from the pressure-sensing mattress C and simultaneously returns to step S10 (performing data recording and calculation results) and executes step S16. Based on the status feedback data obtained from step S15, the system controller A determines whether the pressure-sensing mattress C requires auto turn (for example, when the pressure-sensing mattress C senses that the local pressure reaches a long lying time, an auto turn request is issued to change the lying position of the bedridden person). When receiving the request, the system controller A outputs a task execution signal to the electric turning bed B to execute step S14, causing the electric turning bed B to perform auto turn. When the request is not received, go back to step S10.

In step S17, the system controller A receives status feedback data from the electronic diaper machine D and simultaneously returns to step S10 (executing data recording and calculation results), and executes step S18. Based on the status feedback data of the electronic diaper machine D obtained in step S17, the system controller A determines whether the electronic diaper machine D requires auto turn (for example, if the electronic diaper machine D senses that the bedridden person is excreting when not lying flat, it can issue an auto turn request to restore lying flat position for cleaning). When receiving the request, the system controller A outputs a task execution signal to the electric turning bed B to execute step S14, causing the electric turning bed B to perform auto turn. When the request is not received, go back to step S10.

Figure 8:
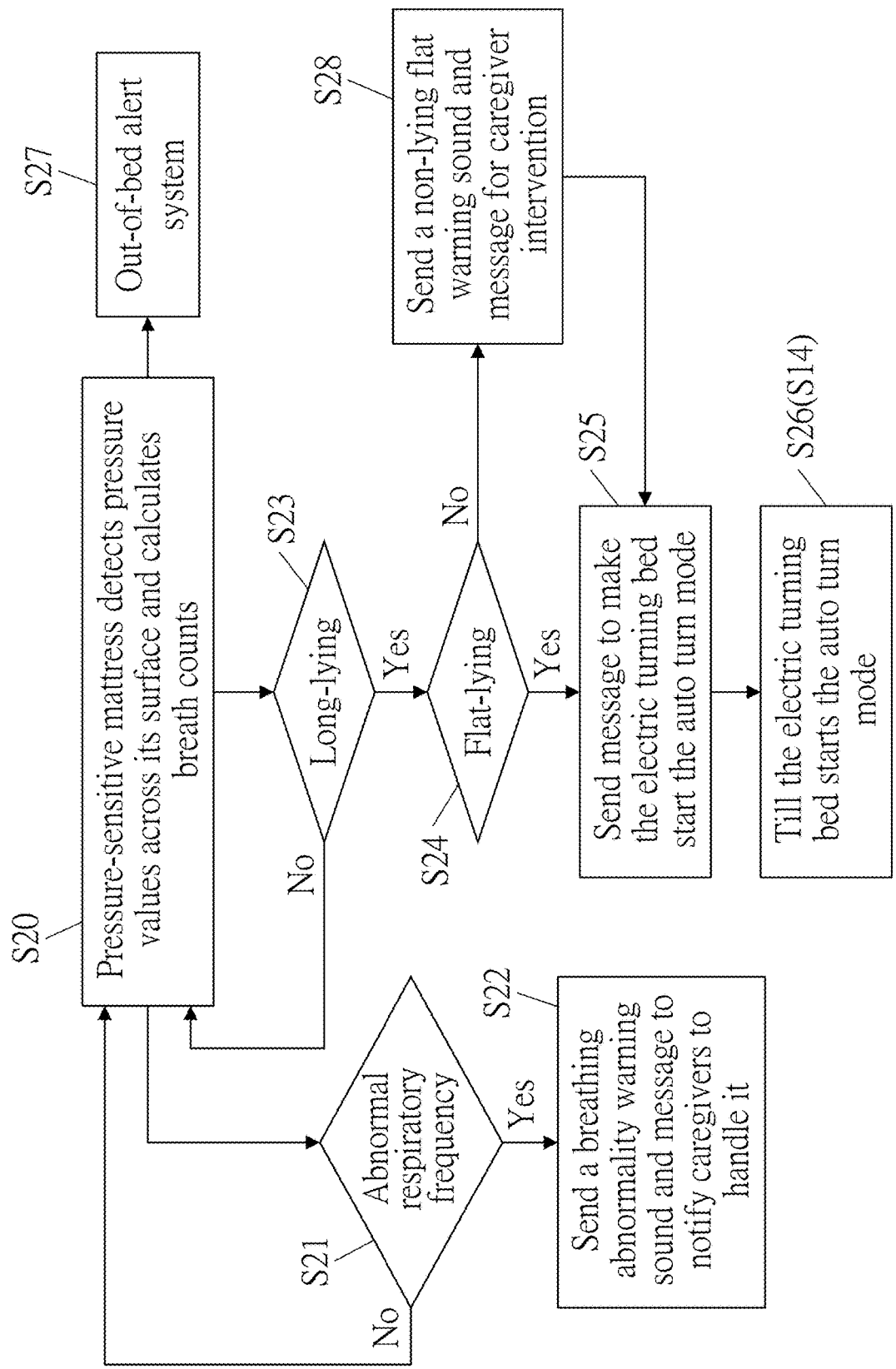
FIG. 8 is a logical schematic diagram of the system controller of the present invention performing a turning task based on the feedback data of the pressure-sensing mattress.

As shown in FIG. 8, the control logic of the system controller A executing the turning task based on the feedback data from the pressure-sensing mattress C. In step S20, the pressure-sensing mattress C continuously detects the pressure values change data of the cushions and calculates the respiratory frequency of the bedridden person based on it. Next, in step S21, the system controller A determines whether an abnormal respiratory frequency has occurred based on the results obtained in step S20. When an abnormality occurs, the system controller A executes step S22 and issues a breathing abnormality warning sound and message to notify caregivers to handle it. When no abnormalities occur, return to step S20.

In step S23, the system controller A determines whether the long-lying time has been reached based on the results obtained in step S20. When it is reached, the system controller A executes step S24 to further determine whether the bedridden person is lying flat. If lying flat, the system controller A executes step S25, sends a task execution signal to the electric turning bed B. Then, the electric turning bed B executes step S26 (i.e. step S14) to make the electric turning bed B perform auto turn. If not lying flat, the system controller A will execute step S28 and issue a non lying flat warning sound and message to notify the caregiver to handle it. Continuing with the judgment in step S24, when the long lying time has not been reached, return to step S20.

Figure 9:
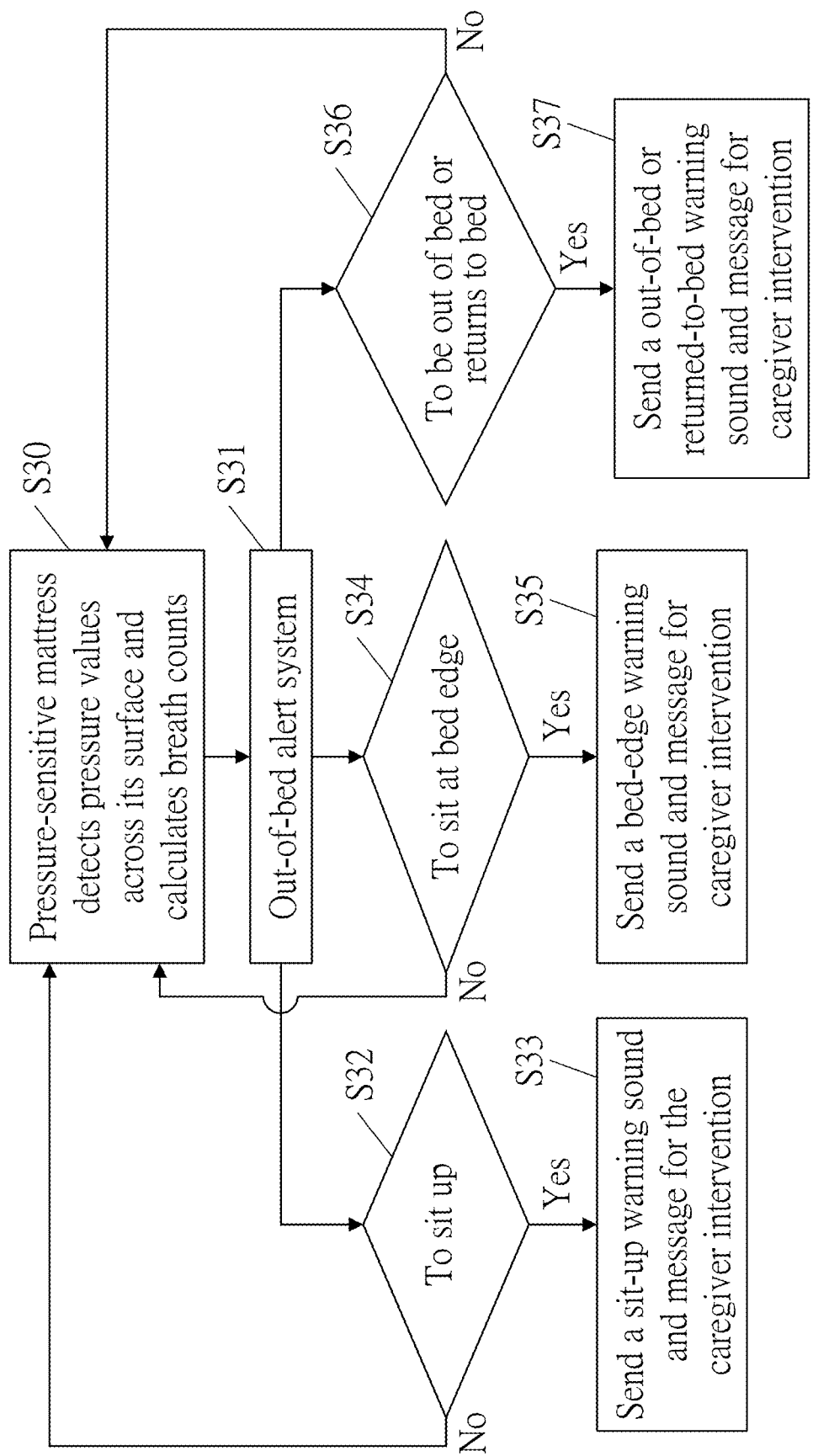
FIG. 9 is a logical schematic diagram of the system controller of the present invention executing a bedridden person leaving the bed warning based on the feedback data of the pressure-sensing mattress.

When the system controller A fails to detect the pressure value change data of the respective cushions of the pressure-sensing mattress C, the system controller A directly executes step S27 to enter the off bed warning system (FIG. 9).

As shown in FIG. 9, the control logic for system controller A to execute the bedridden person off bed warning based on the feedback data of the pressure-sensing mattress is displayed. In steps S30 and S31, when the system controller A fails to detect the pressure value change data of the respective cushions of the pressure-sensing mattress C, the system controller A directly enters the off bed warning system and continues to execute steps S32, S34, and S36 based on the biometric data of the bedridden person to determine the status of the bed user with respect to the electric turning bed B.

In step S32, the system controller A determines whether to sit up based on the bedridden person's biometric data. If so, the system controller A executes step S33 and issues a sit-up warning sound and message for the caregiver intervention. If not, return to step S30.

In step S34, the system controller A determines whether to sit on the edge of the bed based on the biometric data of the bedridden person. If so, the system controller A executes step S35 and issues a sitting on the edge of the bed warning sound and message for caregiver intervention. If not, return to step S30.

In step S36, the system controller A determines whether to leave or return to the bed based on the biometric data of the bedridden person. If so, the system controller A executes step S37, issuing a leaving or returning to the bed warning sound and message to notify the caregiver for processing. If not, return to step S30.

Figure 10:
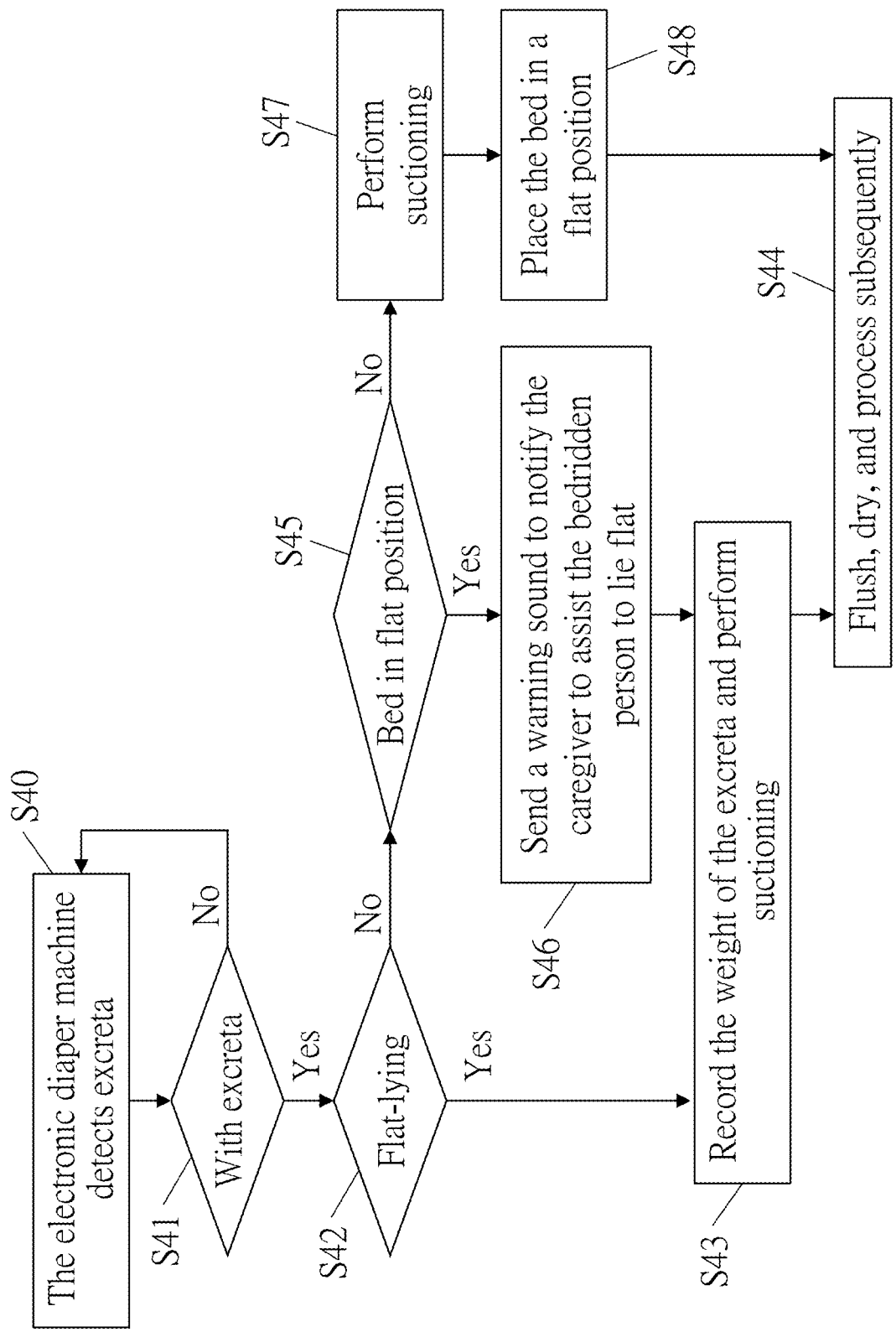
FIG. 10 is a logical schematic diagram of the system controller of the present invention performing cleaning based on the feedback signal of the electronic diaper machine.

As shown in FIG. 10, the control logic of the system controller A executing the cleaning process based on the feedback signal from the electronic diaper machine. In step S40, the electronic diaper machine D continuously senses the status of the bedpan D1. Next, in step S41, the system controller A determines whether there is excrement in the bedpan D1 based on the results obtained in step S40. If not, return to step S40. If yes, the system controller A will execute step S42 to further determine whether the bedridden person is lying flat. If yes, the system controller A will execute step S43 to record the weight of excrement, drive the electronic diaper machine D for suction, and then execute step S44 to drive the electronic diaper machine D for flushing, drying, and subsequent processing. Continuing with the judgment in step S42, if not lying flat, proceed to step S45, the system controller A will further determine whether the bed surface of the electric turning bed B is lying flat. If lying flat, the system controller A will execute step S46, issue a warning sound to notify the caregiver to assist the bedridden person lying flat, and then proceed to steps S43 and S44. Continuing with step S45, if the bed surface is not lying flat, proceed to step S47 where the system controller A drives the electronic diaper machine D for suction. Then, proceed to step S48 to drive the electric turning bed B to enter a lying flat state, and finally proceed to the abovementioned step S44.

In summary, the system of the present invention integrates the system controller with the subsystems such as the electric turning bed, the pressure-sensing mattress, and/or the electronic diaper machine to comprehensively care for patients (bedridden person) who cannot move independently. The system of the present invention ensures the stability, high reliability, and precise control ability of the system through intelligent and automated operation, not only improving the safety and comfort of bedridden people, but also greatly reducing the workload of caregivers, achieving the goal of effectively improving the quality of care services and saving human resources.

What is claimed is:

1. An integrated automatic turning bed system comprising a system controller and a plurality of subsystems connected to the system controller; wherein
the system controller includes a central processing unit (CPU), and a system memory and an AI deep learning module connected to the CPU; the system memory includes a bedridden person database, a movement analysis database, and a movement module database;
the subsystems include at least one electric turning bed, at least one pressure-sensing mattress, and at least one electronic diaper machine, which are connected to the CPU, respectively;
wherein,
the system controller is used to receive and store status feedback data from the electric turning bed, the pressure-sensing mattress, and the electronic diaper machine, the system controller sends out task execution signals to the electric turning bed, the pressure-sensing mattress, and the electronic diaper machine after calculation based on the status feedback data, in order to drive the subsystems to act according to the task execution signals;
the AI deep learning module is used to read the bedridden person database, the movement analysis database, and the movement module database and perform calculations and learning based on the bedridden person database, the movement analysis database, and the movement module database, so as to output and store an AI recommended turning module that is suitable for the current needs of a bedridden person, for prompting caregivers to adapt to the turning mode of the bedridden person.

2. The integrated automatic turning bed system as claimed in claim 1, wherein the electric turning bed includes a main frame, an actuating device, a lifting base frame, and a tilting frame; the main frame includes twelve sub-frames; the twelve sub-frames of the main frame are a back frame, a seat frame, a leg frame, and a foot frame corresponding to respective parts of the human body, as well as two back side frames, two seat side frames, two leg side frames, and two foot side frames disposed at two sides of the respective part-frames; the tilting frame is located on the back frame; the lifting base frame is located below the main frame, the actuating device includes twelve main-frame actuators independently connected to the twelve sub-frames, a base-frame actuator independently connected to the lifting base frame, and a tilting-frame actuator independently connected to the tilting frame; each of the main-frame actuators, the base-frame actuator, and the tilting-frame actuator includes a frame motion sensing unit to detect and output status feedback data corresponding to the twelve sub-frames of the main frame, the lifting base frame, and the tilting frame;
the CPU is connected to the frame motion sensing units, the main-frame actuators, the base-frame actuator, and the tilting-frame actuator; so that the CPU receives the status feedback data and outputs task execution signals to drive the main-frame actuators, the base-frame actuators, and/or the tilting-frame actuators to operate.

3. The integrated automatic turning bed system as claimed in claim 2, wherein the status feedback data output from the main-frame actuators, the base-frame actuators, and/or the tilting-frame actuators include displacement distance and/or displacement angle of the twelve sub-frames of the main frame, the lifting base frame, and the tilting frame; so that the CPU outputs, by calculation based on the displacement distance and/or displacement angle, task execution signals to drive the main frame, the lifting base frame, and the tilting frame to operate.

4. The integrated automatic turning bed system as claimed in claim 2, wherein the pressure-sensing mattress is disposed on the electric turning bed, and the pressure-sensing mattress is a foldable mattress and includes twelve cushions correspondingly disposed to the twelve sub-frames of the main frame, inside each of the twelve cushions is provided a pressure sensor to detect and output status feedback data corresponding to the twelve cushions;
the CPU obtains biometric data of the bedridden person based on the status feedback data; so that the CPU outputs, by calculation based on the biometric data, task execution signals to drive the main frame, the lifting base frame, and the tilting frame to operate.

5. The integrated automatic turning bed system as claimed in claim 4, wherein the status feedback data from the respective pressure sensors include pressure sensing data of the twelve cushions; so that the CPU calculates the biometric data of the bedridden person based on the status feedback data, and the CPU calculates and outputs task execution signals that drive the main frame, the lifting base frame, and/or the tilting frame to operate.

6. The integrated automatic turning bed system as claimed in claim 5, wherein the biometric data include the pressure values of the cushions of the pressure-sensing mattress, and respiratory frequency, heartbeat frequency, sleep analysis, and long-lying analysis of the bedridden person.

7. The integrated automatic turning bed system as claimed in claim 4, wherein the status feedback data from the respective pressure sensors include pressure sensing data of the twelve cushions; the pressure-sensing mattress includes a pressure state analysis module connected to the respective pressure sensors, the pressure state analysis module calculates and outputs the biometric data of the bedridden person based on the pressure sensing data, and the CPU receives and outputs task execution signals that drive the main frame, the lifting base frame, and/or the tilting frame to operate based on the biometric data.

8. The integrated automatic turning bed system as claimed in claim 7, wherein the biometric data include the pressure values of the cushions of the pressure-sensing mattress, and respiratory frequency, heartbeat frequency, sleep analysis, and long-lying analysis of the bedridden person.

9. The integrated automatic turning bed system as claimed in claim 4, wherein the electronic diaper machine includes a bedpan, an excreta sensor, a suction device, and a rinse device;
the bedpan is movably disposed on the pressure-sensing mattress;
the excreta sensor is installed in the bedpan to detect the presence of excrement and output excreta detection data;
the suction device is connected to the bedpan to suction excrement out of the bedpan;
the rinse device is connected to the bedpan and outputs washing liquid for cleaning;
the status feedback data of the electronic diaper machine include excreta detection data output from the excreta sensor, suction status data output from the suction device, and rinse status data from the rinse device; the CPU is connected to the excreta sensor, the suction device, and the rinse device, and the CPU receives the excreta detection data, the suction status data and the rinse status data and calculates and outputs task execution signals to drive the suction device and/or the rinse device to operate.

10. The integrated automatic turning bed system as claimed in claim 2, wherein the system controller further includes a human-machine interface module; the human-machine interface module includes a plurality of bed frame adjustment keys, and the bed frame adjustment keys are used to adjust the amplitude of single or combined movements.

11. The integrated automatic turning bed system as claimed in claim 10, wherein the human-machine interface module further includes a movement lock key to lock or unlock the movement of the electric turning bed.

12. The integrated automatic turning bed system as claimed in claim 1, wherein the electronic diaper machine includes a bedpan, an excreta sensor, a suction device, and a rinse device;
the bedpan is movably disposed on the pressure-sensing mattress;
the excreta sensor is installed in the bedpan to detect the presence of excrement and output excreta detection data;
the suction device is connected to the bedpan to suction excrement out of the bedpan;
the rinse device is connected to the bedpan and outputs washing liquid for cleaning;
the status feedback data of the electronic diaper machine include excreta detection data output from the excreta sensor, suction status data output from the suction device, and rinse status data from the rinse device; the CPU is connected to the excreta sensor, the suction device, and the rinse device, and the CPU receives the excreta detection data, the suction status data and the rinse status data and calculates and outputs task execution signals to drive the suction device and/or the rinse device to operate.

13. The integrated automatic turning bed system as claimed in claim 1, wherein the system controller is in communication with a monitoring center, the monitoring center is equipped with a server and an electronic whiteboard connected to the server;

the server is in communication with the CPU to store status feedback data received by the CPU, data obtained by the CPU or the AI deep learning module, and the task execution signals output from the CPU;

the electronic whiteboard is connected to the server, and displays at least one monitoring display area corresponding to the current status of the electric turning bed, and the monitoring display area includes a bedridden person code, monitoring status fields, and status prompt fields.

14. The integrated automatic turning bed system as claimed in claim 13, wherein the system controller and the monitoring center are connected to a cloud server for data transmission, communication, storage, and/or computation; the cloud server is used to store status feedback data received by the CPU, data obtained by the CPU or the AI deep learning module, and the task execution signals output from the CPU.

15. The integrated automatic turning bed system as claimed in claim 14, wherein the AI deep learning module is connected to the cloud server to read the status feedback data of the subsystems stored in the cloud server, and synchronously feed back data of the AI recommended turning mode obtained from the operation based on the status feedback data of the subsystems to the cloud server, the system memory, and the server of the monitoring center for storage.

16. The integrated automatic turning bed system as claimed in claim 1, wherein the system controller further includes a human-machine interface module; the human-machine interface module includes an information display area that is used to display the current status information of the bedridden person and warning information and suggestion information provided by the system controller.

17. The integrated automatic turning bed system as claimed in claim 16, wherein the human-machine interface module includes a language switch key to switch display language of the information display area.

18. The integrated automatic turning bed system as claimed in claim 1, wherein the system controller further includes a human-machine interface module; the human-machine interface module includes an emergency operation key for automatically regulating the electric turning bed to form a state suitable for emergency operation according to the standard specifications of electrical medical equipment IEC60601-2-52 and CNS 15521.

\* \* \* \* \*